US00PP20086P2

(12) United States Plant Patent
Fitzgerald

(10) Patent No.: US PP20,086 P2
(45) Date of Patent: Jun. 9, 2009

(54) ***SALVIA* PLANT NAMED 'FLOSALG03'**

(50) Latin Name: *Salvia greggii*
Varietal Denomination: Flosalg03

(75) Inventor: Doug Fitzgerald, Cape Town (ZA)

(73) Assignee: Floranova Ltd., Derreham, Norfolk (GB)

( * ) Notice: Subject to any disclaimer, the term of this patent is extended or adjusted under 35 U.S.C. 154(b) by 0 days.

(21) Appl. No.: 12/077,203

(22) Filed: Mar. 17, 2008

(51) Int. Cl.
*A01H 5/00* (2006.01)

(52) U.S. Cl. ..... Plt./475
(58) Field of Classification Search ..... Plt./463, Plt./475
See application file for complete search history.

*Primary Examiner*—S. B. McCormick Ewoldt
(74) *Attorney, Agent, or Firm*—C. A. Whealy

(57) ABSTRACT

A new and distinct cultivar of *Salvia* plant named 'Flosalg03', characterized by its compact and upright plant habit; freely branching habit; freely flowering habit; long flowering period; and purple violet-colored flowers.

1 Drawing Sheet

Botanical designation: *Salvia greggii.*
Cultivar denomination: 'Flosalg03'.

BACKGROUND OF THE INVENTION

The present invention relates to a new and distinct cultivar of *Salvia,* botanically known as *Salvia greggii* and hereinafter referred to by the name 'Flosalg03'.

The new *Salvia* is a product of a planned breeding program conducted by the Inventor in Gauteng, South Africa. The objective of the program is to create and develop new compact *Salvia* cultivars with a long and freely flowering habit.

The new *Salvia* originated from a cross-pollination by the Inventor in January, 2000 of a proprietary selection of *Salvia greggii* identified as code number SG7287, not patented, as the female, or seed, parent with a proprietary selection of *Salvia greggii* identified as code number SG7894, not patented, as the male, or pollen, parent. The new *Salvia* was discovered and selected by the Inventor as a single flowering plant within the progeny of the stated cross-pollination in a controlled environment in Gauteng, South Africa in October, 2000.

Asexual reproduction of the new cultivar by vegetative cuttings in Gauteng, South Africa since April, 2001, has shown that the unique features of this new *Salvia* are stable and reproduced true to type in successive generations.

SUMMARY OF THE INVENTION

Plants of the cultivar Flosalg03 have not been observed under all possible environmental conditions. The phenotype may vary somewhat with variations in environment such as temperature and light intensity without, however, any variance in genotype.

The following traits have been repeatedly observed and are determined to be the unique characteristics of 'Flosalg03'. These characteristics in combination distinguish 'Flosalg03' as a new and distinct cultivar:

1. Compact and upright plant habit.
2. Freely branching habit.

3. Freely flowering habit.
4. Long flowering period.
5. Purple violet-colored flowers.

Plants of the new *Salvia* differ from plants of the female parent selection in the following characteristics:

1. Plants of the new *Salvia* are taller than plants of the female parent selection.
2. Plants of the new *Salvia* are not as freely branching as plants of the female parent selection.
3. Plants of the new *Salvia* and the female parent selection differ in flower color as plants of the female parent selection have white-colored flowers.

Plants of the new *Salvia* differ from plants of the male parent selection in the following characteristics:

1. Plants of the new *Salvia* are shorter than plants of the male parent selection.
2. Plants of the new *Salvia* are more freely branching than plants of the male parent selection.
3. Plants of the new *Salvia* and the male parent selection differ in flower color as plants of the male parent selection have dark blue-colored flowers.

Plants of the new *Salvia* can be compared to plants of the cultivar Navaho Deep Purple, not patented. In side-by-side comparisons conducted by the Inventor in Lompoc, Calif., plants of the new *Salvia* differed from plants of the cultivar Navaho Deep Purple in the following characteristics:

1. Plants of the new *Salvia* were more compact than plants of the cultivar Navaho Deep Purple.
2. Plants of the new *Salvia* were more freely branching than plants of the cultivar Navaho Deep Purple.
3. Plants of the new *Salvia* flowered for a longer period of time than plants of the cultivar Navaho Deep Purple.
4. Plants of the new *Salvia* and the cultivar Navaho Deep Purple differed in flower color as plants of the cultivar Navaho Deep Purple had dark purple-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Salvia*.

The photograph at the bottom of the sheet comprises a side perspective view of a typical flowering plant of 'Flosalg03' grown in a container.

The photograph at the top of the sheet is a close-up view of a typical flower of 'Flosalg03'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown under conditions which closely approximate commercial production conditions during the winter and spring in a polycarbonate-covered greenhouse in Lompoc, Calif. During the production of the plants, day temperatures ranged from 21° C. to 24° C., night temperatures ranged from 16° C. to 18° C. and light levels ranged from 4,000 to 8,000 foot-candles. Plants were pinched one time about four weeks after planting. Plants used for the photographs and description were about 18 weeks old.

Botanical classification: *Salvia greggii* cultivar Flosalg03.

Parentage:

*Female, or seed, parent.*—Proprietary selection of *Salvia greggii* identified as code number SG7287, not patented.

*Male, or pollen, parent.*—Proprietary selection of *Salvia greggii* identified as code number SG7894, not patented.

Propagation:

*Type cutting.*—Vegetative cuttings.

*Time to initiate roots, summer.*—About 12 to 15 days at 22° C.

*Time to initiate roots, winter.*—About 12 to 18 days at 22° C.

*Time to produce a rooted young plant, summer.*—About 30 to 40 days at 22° C.

*Time to produce a rooted young plant, winter.*—About 35 to 45 days at 18° C.

*Root description.*—Fine, fibrous; white in color.

*Rooting habit.*—Freely branching; moderately dense.

Plant description:

*Form.*—Herbaceous perennial subshrub. Upright plant form; narrow inverted triangle. Freely branching habit with about six main stems; pinching enhances branch development; vigorous growth habit. Flowers arranged in verticillasters on spikes.

*Plant height.*—About 28 cm.

*Plant width.*—About 25 cm.

*Lateral branch description.*—Length: About 20 cm. Diameter: About 2 mm. Internode length: About 2 cm to 2.5 cm. Strength: Strong. Aspect: Mostly upright. Texture: Young stems with minute pubescence; mature stems, woody and glabrous. Color, young stems: Close to 147B. Color, mature stems: Close to 200D.

Foliage description:

*Arrangement.*—Opposite, simple.

*Length.*—About 2.8 cm.

*Width.*—About 1.3 cm.

*Shape.*—Elliptic.

*Apex.*'Broadly acute.

*Base.*—Attenuate to obtuse.

*Margin.*—Entire.

*Texture, upper and lower surfaces.*—Smooth, glabrous.

*Venation pattern.*—Pinnate; arcuate.

*Color.*—Developing foliage, upper surface: Close to 144A. Developing foliage, lower surface: Close to 147B. Fully expanded foliage, upper surface: Close to 147A; venation, close to 147B. Fully expanded foliage, lower surface: Close to 147B; venation, close to 147B.

*Petiole length.*—About 7 mm.

*Petiole diameter.*—About 1 mm.

*Petiole texture, upper and lower surfaces.*—Smooth, glabrous.

*Petiole color, upper and lower surfaces.*—Close to 147C.

Flower description:

*Flower arrangement and shape.*—Single bilabiate flowers arranged in verticillasters on spikes; flowers face mostly outwardly. Freely flowering habit, about 39 flowers per inflorescence.

*Natural flowering season.*—Continuous flowering from spring through summer to central California.

*Flower longevity on the plant.*—About four to five days; flowers not persistent.

*Flower buds.*—Length: About 9 mm. Diameter: About 4 mm. Shape: Oblong. Color: Close to 83B.

*Inflorescence size.*—Length: About 9 cm. Diameter: About 4.3 cm.

*Flowers.*—Diameter: About 1.6 cm by 1.9 cm. Depth (height): About 2.3 cm.

*Petals.*—Arrangement: Five; upper two fused in an upper banner lip and lower three fused in a lower protruding lip; all five fused at the base. Shape, upper lip: Elongate with acute apex and entire margin. Shape, lower lip: Rounded with rounded apex and entire margin. Length, upper lip: About 1.2 cm. Length, lower lip: About 1.5 cm. Width, upper lip: About 3 mm. Width, lower lip: About 1.6 cm. Texture, upper lip, upper and lower surfaces: Pubescent. Texture, lower lip, upper and lower surfaces: Smooth, glabrous. Color, upper and lower lips: When opening, upper surface: Brighter than 77A. When opening, lower surface: More grey than 77A. Fully opened, upper surface: Close to 80B. Fully opened, lower surface: Close to 82B to 82C. Throat: Close to 69B. Tube: Close to between 82B to 82C and 77A.

*Sepals.*—Arrangement: Three fused into a tube. Shape: Elliptic with acute apex and entire margin. Length: About 6 mm. Width: About 3 mm. Texture, inner surface: Smooth, glabrous. Texture, outer surface: Pubescent. Color, when opening and fully opened, inner surface: Close to 147C. Color, when opening and fully opened, outer surface: Close to 79B.

*Peduncles.*—Strength: Strong. Length: About 2.5 cm. Diameter: About 1.5 mm. Aspect: Erect. Texture: Pubescent. Color: Close to 146B.

*Pedicels.*—Strength: Strong. Length: About 4 mm. Diameter: About 1 mm. Aspect: About 30° to 45° from peduncle axis. Texture: Pubescent. Color: Close to 146A.

*Reproductive organs.*—Stamens: Quantity per flower: Two. Anther shape: Oval, elongated. Anther length:

About 2 mm. Anther color: Close to 164B. Pollen amount: Scarce. Pollen color: Close to 13A. Pistils: Quantity per flower: One. Pistil length: About 2.9 cm. Stigma shape: Bi-parted. Stigma color: Close to 77A. Style length: About 2.4 cm. Style color: Close to 76B. Ovary color: Close to 145D. Seed/fruit: Seed and fruit production has not been observed.

Disease/pest resistance: Plants of the new *Salvia* have not been noted to be resistant to pathogens and pests common to *Salvia*.

Garden performance: Plants of the new *Salvia* have exhibited good tolerance to rain and wind and have been observed to tolerate temperatures from about 4° C. to about 40° C.

It is claimed:

1. A new and distinct *Salvia* plant named 'Flosalg03' as illustrated and described.

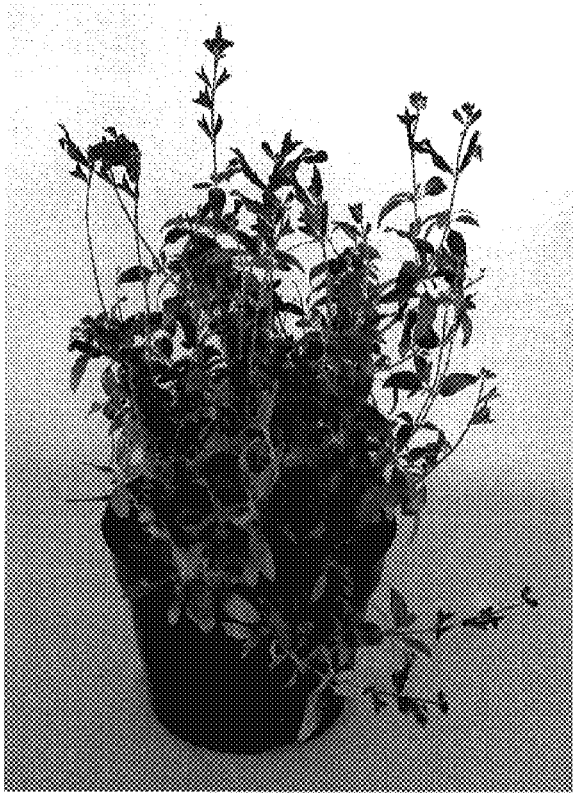
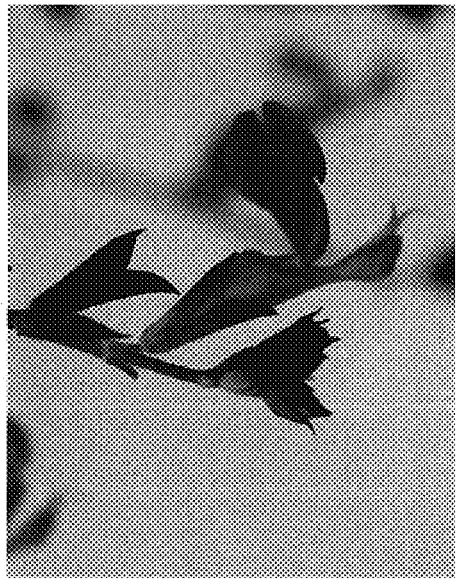

* * * * *